United States Patent [19]

Haagensen, Jr.

[11] 4,440,863

[45] Apr. 3, 1984

[54] BREAST CYST FLUID PROTEIN ASSAY

[75] Inventor: Darrow E. Haagensen, Jr., Newtonville, Mass.

[73] Assignee: Duke University, Durham, N.C.

[21] Appl. No.: 292,369

[22] Filed: Aug. 13, 1981

Related U.S. Application Data

[60] Continuation-in-part of Ser. No. 102,095, Dec. 10, 1979, which is a division of Ser. No. 880,257, Feb. 22, 1978, Pat. No. 4,229,426.

[51] Int. Cl.³ .................... G01N 33/54; G01N 33/58; G01N 33/60; C07C 7/00
[52] U.S. Cl. .................................. 436/539; 436/542; 436/543; 436/544; 436/545; 436/804; 436/813; 436/811; 260/112 R; 260/112 B; 260/112.5 R
[58] Field of Search ............ 424/1; 436/539, 542–545, 436/804, 813, 811; 260/112 R, 112 B, 112.5 R

[56] References Cited

U.S. PATENT DOCUMENTS 4,229,426 10/1980 Haagensen, Jr. .................. 424/1

OTHER PUBLICATIONS

Haagensen, Jr. et al., Annals of Surgery, 185(3), 279-285 (1977).
Haagensen, Jr. et al., J. Natl. Cancer Inst., 62(2), 239-247 (1979).

*Primary Examiner*—Christine M. Nucker
*Attorney, Agent, or Firm*—Jon S. Saxe; George M. Gould; John J. Maitner

[57] ABSTRACT

This disclosure relates to assay of a glycoprotein component of human breast gross cystic disease fluid which has been designated GCDFP-15. This material is a useful marker in monitoring the efficacy of therapy in women with metastatic breast carcinoma and also in determining the maturity of the fetus in pregnant women. The assay for GCDEP-15 can also be used in conjunction with other assays for breast carcinoma such as an assay for carcinoembryonic antigen (CEA) whereby the utilization of both tests is more effective in monitoring for recurrence of disease than using either assay alone.

5 Claims, No Drawings

BREAST CYST FLUID PROTEIN ASSAY

This application is a continuation-in-part of Ser. No. 102,095, filed Dec. 10, 1979, which is a divisional of Ser. No. 880,257, filed Feb. 22, 1978, now U.S. Pat. No. 4,229,426.

BACKGROUND OF THE INVENTION

Human breast gross cystic disease has been investigated by C. D. Haagensen, *Diseases of the Breast*, Second Edition, Chapter 7, Cystic Disease of the Breast (W. B. Saunders, Philadelphia, 1971). It has been found that patients who develop this disease have approximately a four-fold increased incidence of breast carcinoma above normal. This data suggests a significant link between breast carcinoma and gross cystic disease.

Up to the present, biochemical analysis of breast cystic disease fluid has been limited and incomplete. High levels of CEA have been found in the fluid as well as high potassium levels indicating an intracellular-like ionic consistency. See, in this regard, two papers by J. Fleisher and coworkers:

Clin. Chem., 20/1, 41 (1974); and
Memorial Sloan-Kettering Cancer Center Clinical Bulletin, pages 94–97 (1974).

A report of clinical evaluation of the GCDFP-15 immunoassay of the present invention has been published in Ann. Surg., 185, 279 (1977). Methods for diagnosing, identifying and detecting carcinoembryonic antigen are disclosed in U.S. Pat. No. 3,663,684. An assay for the A and B components of carcinoembryonic antigen is disclosed in U.S. Pat. No. 3,697,638.

DESCRIPTION OF THE INVENTION

The present invention relates to the discovery that a specific glycoprotein isolated from human gross cystic disease fluid can serve as a marker detectable in the systemic circulation of patients with breast carcinoma. Such glycoprotein can be conveniently detected by immunoassay techniques particularly by radioimmunoassay.

Gross cystic disease fluid appears to be a unique secretion from breast epithelial cells, probably in response to abnormal hormonal stimulation. Of significant importance is the relative uniformity of gross cystic disease fluid proteins (GCDFP) as judged by sodium dodecyl sulfate (SDS) and acrylamide gel analysis from patient to patient indicating a common pathophysiological etiology. Four major component proteins appear present in all GCDFP samples. Such proteins are designated GCDFP-70, GCDFP-44, GCDFP-24 and GCDFP-15.

The GCDFP-70 component has been found to be immunologically identical to human albumin. It is present in trace amounts in GCDFP relative to plasma, approximately 1/100th the plasma concentration.

The GCDFP-44 component has been found to be immunologically identical to plasma Zn-alpha$_2$-glycoprotein. The GCDFP-44 component is found at an approximately fifty-fold higher concentration in GCD fluid than in plasma.

The GCDFP-24 component appears to be a progesterone binding glycoprotein and is immunologically identical to an unidentified human plasma component which is present in Cohn Fraction VI. The GCDFP-24 component is at approximately a 100-fold higher concentration in GCD fluid (10–50 mg/ml) than the immunologically cross identical component of human plasma. This GCDFP-24 component has been described by Pearlman and co-workers, cf. J. Biol. Chem. 248/16, 5736 (1973); J. Endocrinology 75/3, p. 19 (1977).

Finally, unlike the other major glycoprotein components of GCD fluid, the GCDFP-15 component is not immunologically identical to any components of plasma as determined by Ouchterlony analysis. However, GCDFP-15 was found to have immunological cross-identity with a component present in both human milk and human saliva. The GCDFP-15 component thus represents a specific epithelial cell secretion. Therefore this GCDFP-15 component is particularly suitable to serve as a plasma marker for breast carcinoma monitoring due to carcinoma cell secretions into the systemic circulation.

The isolation of GCDFP-15 from human gross cystic disease fluids can be accomplished by utilizing conventional protein isolation techniques. Thus, GCD fluid samples after ultracentrifugation may be chromatographed on a column of Sephadex G-200 which results in two main elution peaks corresponding to molecular sizes of 140,000 (Pool I) and 70,000 (Pool II). The Sephadex G-200 Pool II material is then further fractionated by Hydroxylapatite column chromatography and DEAE-Agarose step gradient. Purification of the GCDFP-15 component is achieved by recycling the desired eluate through the DEAE-Agarose step gradient.

More specifically, the purification of GCDFP-15 can be carried out as follows. Breast GCD fluid was obtained by needle aspiration from women under treatment for gross cystic disease. The GCD fluid specimens were stored at $-10°$ C. Initial processing of specimens consisted of ultracentrifugation at $160,000 \times G$ for one hour.

Fifteen separate GCD fluid samples were individually column chromatographed on Sephadex G-200 (Pharmacia) in a $2.6 \times 80$ cm column at $10°$ C. Ammonium acetate buffer, 0.1 M, pH 6.75, was used as the eluent with an elution rate of 16 ml/hr by gravity flow. Absorbance of eluted fractions was determined at 280 nm. Each sample gave a slightly different elution profile. Several of the samples demonstrated two separate peaks of approximately 140,000 and 70,000 molecular size. The fifteen individual Sephadex G-200 separated samples were pooled into regions I and II approximating these two peaks.

The Sephadex G-200 region II pool was further fractionated by Hydroxylapatite chromatography using Hydroxylapatite (Biorad) in a $1.5 \times 30$ cm column. The Hydroxylapatite was pre-equilibrated in 0.01 M NaH$_2$PO$_4$ buffer, pH 4.8. Samples were pre-equilibrated in the same buffer by dialysis. Elution of the column was carried out with sequential buffer applications of 0.01 M, pH 4,8; 0.15 M, pH 4.8; and 0.15 M, pH 8.6 NaH$_2$PO$_4$ buffer. Each buffer solution product volume was 200 ml.

The 0.15 M NaH$_2$PO$_4$, pH 8.6 eluate was placed on a DEAE-Agarose (Biorad) $1.5 \times 30$ cm column. The DEAE-Agarose was pre-equilibrated in 0.05 M NaH$_2$PO$_4$, pH 4.8 buffer. Elution of the column was carried out with sequential buffer applications of 0.05 M, 0.075 M and 0.5 M NaH$_2$PO$_4$, pH 4.8 buffer. Each buffer solution product volume was 200 ml.

The 0.5 M NaH$_2$PO$_4$, pH 4.8 eluent was recycled on the DEAE-Agarose step gradient for purification of the GCDFP-15 component.

The purified GCDFP-15 thus obtained appears to have an elution volume molecular size of approximately 70,000 daltons for the concentrated form and 40,000 deltons when it is highly diluted. Thus, this component appears to be in a polymeric form in gross cystic disease fluid. The calculated monomer size obtained by SDS-acrylamide electrophoresis is approximately 15,000 daltons. Sulfhydryl reducing agents are not needed to produce the monomer formed GCDFP-15 on SDS-acrylamide electrophoresis.

An attempt to determine the amino acid sequence of GCDFP-15 by direct gas phase techniques was unsuccessful since the N-terminal end of the glycoprotein was apparently blocked. Cleavage of GCDFP-15 with cyanogen bromide produced two peptide fragments one of which is blocked. The calculated molecular size of one of the peptide fragments from the cyanogen bromide cleavage is approximately 12,500 daltons as determined by SDS-acrylamide electrophoresis. The partial amino acid sequence of this peptide fragment as determined by gas phase techniques is as follows:

$$\underset{}{H_2N}-Val-Val-Lys-Thr-Tyr-Leu-Ile-Ser-Ser-Ile-Pro-Leu-\overset{10}{}$$
$$Gln-Gly-Ala-Phe-Asn-Tyr-Lys-Tyr-Thr-Ala-(Cys)-Leu-(Cys)-\overset{20}{}\overset{30}{}$$
$$Asp-Asp-Asn-Pro-Lys-Thr-Phe-Tyr-Trp-Asp-Phe-Tyr-Thr-(Gln)-\overset{39}{}$$

( ) indicate possible derivitization

Cyanogen bromide cleavage of purified GCDFP-15 is carried out by first lyophilizing the protein then adding sufficient distilled water to the lyophilizing material to produce a volume of 1.5 ml. To this solution is added 75 mM of 1,4-dithiothreitol (DTT), followed by heating at 37° C. for 1 hour. Excess DTT is removed by dialysis against two changes of two liters water. The protein cleavage reaction is carried out by adding 7.8 ml of 97–99% formic acid containing 500 mg cyanogen bromide followed by incubation at 25° C. for 16 hours. Cyanogen bromide is removed by dialyzing the reaction mixture overnight against two changes of 2 liters water. The resulting cyanogen bromide protein cleavage fragments are lyophilized then sufficient distilled water is added to produce a sample volume of 2.5 ml. The protein cleavage fragments are reduced by adding 75 mM DTT followed by incubation at 37° C. for 1 hour. A 250 μl portion is removed from the sample and mixed with 250 μl of N-ethylmopholine. To this solution is added 375 μl 5-dimethylamino-1-naphthylene sulfonylchloride (25 mg/ml in dimethyl formamide) followed by vortexing. The dansylation reaction is allowed to proceed at room temperature for 2 hours then the dansylated peptides are precipitated by adding 3 ml of acetone followed by centrifugation for 5 minutes at approximately 1,000 RPM. The precipitated peptides are re-washed three times with acetone by the above procedure. After the final centrifugation spin, the peptide precipitate is solubilized by addition of 250 μl of 2% SDS and dialyzed overnight against 2% SDS. Lysine, 1 mg, is added to the dansylated fragments before mixing these peptide fragments with the original fragments. Sodium thioglycollate, 5 mM, and 10% glycerol is added to the final sample just prior to loading 10% of the sample onto polyacrylamide gel electrophoresis slab.

The acrylamide gels utilized in the electrophoresis are prepared in the following manner. A 12% acrylamide gel is prepared by adding 7.5 ml of a 40% acrylamide solution (38.8% acrylamide and 1.2% methylene-bis-acrylamide) to 11.25 ml water and 6.25 ml buffer [1.5 M tris (hydroxymethyl) aminomethane, pH 8.8 and 0.4% SDS]. To this solution is added 0.08 ml ammonium persulfate and 8 μl of N,N,N′,N′-tetramethylethylenediamine. A 22% acrylamide gel is prepared by adding 13.75 ml of 40% acrylamide solution (38.8% acrylamide and 1.2% methylene-bis-acrylamide) to 5.0 ml water and 6.25 ml buffer [1.5 M tris (hydroxymethyl) aminomethane, pH 8.8 and 0.4% SDS]. To this solution is added 0.08 ml ammonium persulfate and 8 μl N,N,N′,N′-tetramethylethylenediamine. An acrylamide gel gradient slab from 12% to 22% is prepared from the above two solutions.

Electrophoresis was carried out by loading 10% of the GCDFP-15 cyanogen bromide peptides cleavage fragments containing the dansylated fragments as markers onto the above acrylamide gradient slab. The protein solution was placed into 15 wells containing 25 μl each which represented a total of about 10% of the original cyanogen bromide fragments. The electrophoresis buffer contained 47.6 g glycine, 12.12 g of tris (hydroxymethyl) aminomethane and sufficient distilled water to make 4 liters. The electrophoresis was performed at 25 V overnight until the dye track moved to approximately ⅛ cm from the bottom of the gel.

After electrophoresis, two distinct fluorescent bands (dansylated fragments) were observed in the gel by ultraviolet light; both were marked with India ink. The gels were stained for 1 hour at room temperature in staining solution containing 25% isopropanol, 10% acetic acid and 0.25% Coomassie Brilliant Blue dye, then destained in a solution containing 25% methanol and 10% acetic acid.

The 12,500 dalton band in the gel was cut out for elution and sequence analysis. A 3.5K membrane was cleaned by washing twice in 1% NaHCO₃ at 60° C. then washing once in 1% SDS at 60° C. before use. The cut out gel piece was placed in the negative side of the elutor with 1 ml of 0.2 M Tris acetate pH 8.0, 1% SDS and 1 mg DTT and incubated at room temperature for 2 hours before starting the elution. After adding 0.05 M Tris acetate pH 7.8 and 0.1% SDS to both sides of the elution chamber, the sample was eluted at 50 v for 2 hours. The outside chamber buffer was changed and elution then continued at 50 v for 2 days. The eluted samples were removed and placed in a small elutor to concentrate to 100 μl followed by analyses on the amino acid sequenator.

Antibodies selective to GCDFP-15 can be elicited by injecting the purified component into a suitable animal host. Suitable animal hosts include rabbits, guinea pigs, horses, sheep, goats and the like. Rabbits represent a preferred animal host. The GCDFP-15 can be injected in a suitable fluid vehicle such as incomplete Freund's adjuvant. Multiple immunizations are usually required in order to achieve desirable antibody levels in the host's serum. Bleeding of the host animal provides the desired antiserum.

In a specific embodiment, antiserum containing antibodies selective to GCDFP-15 was prepared in rabbits. The rabbits were injected weekly with a 1.0 ml. volume of purified GCDFP-15 at 1.0 mg/ml in 50% incomplete Freund's adjuvant. After six immunizations, rabbits were injected biweekly and bled by ear vein prior to each injection. Absorption of antiserum was carried out by addition of the absorbing antigen directly to a specific quantity of antiserum followed by incubation at 10°

C. for 24 hours. The precipitate was removed by centrifugation at 2,000 rpm for 20 minutes at 10° C.

Radiolabelled GCDFP-15 is readily prepared from the purified protein by procedures well known in the art. Suitable radiolabelled derivatives of GCDFP-15 include $^3$H-, $^{14}$C-, $^{131}$I- and $^{125}$I-. Particularly preferred is the $^{125}$I-derivative which is produced by radiolabelling the compound using the method of Hunter and Greenwood, Nature, 194, 495 (1962).

A suitable radioimmunoassay for the GCDFP-15 component may be performed in the following manner. Polypropylene tubes are used for the reaction. 500 µl of 0.1 M ammonium acetate buffer, pH 6.75, is added to each tube. The GCDFP-15 antigen standard for the radioimmunoassay is a 1:10,000 dilution of a 0.5 mg/ml solution of purified GCDFP-15. This standard is made up in 0.1 M ammonium acetate buffer, pH 6.75, containing 1 mg/ml crystallized human albumin. For the assay, five antigen inhibition curve tubes (in duplicate) receive 0 µl, 25 µl, 50 µl, 75 µl and 100 µl, respectively, of the GCDFP-15 antigen standard which is equivalent to 0 ng, 1.25 ng., 2.5 ng., 3.75 ng. and 5 ng. of the GCDFP-15.

Each of the antigen inhibition curve tubes receives 50 µl of a 80 mg/ml solution of bovine plasma. Experimental tubes (in duplicate) receive 50 µl of plasma sample. All assay tubes receive 100 µl of a 1:2,000 dilution of antiserum. The assay tubes are incubated at 10° C. for 18 hours followed by the addition to each tube of 100 µl of a 1:10 dilution of stock $^{125}$I-radiolabelled GCDFP-15. The tubes are then incubated at room temperature for five hours. The reaction is stopped by the addition to each tube of 6.5 ml.of zirconyl phosphate gel (Z-gel) suspension in 0.1 M ammonium acetate buffer, pH 6.75 (equivalent to 0.5 ml. of Z-gel pellet). Zirconyl phosphate gel is prepared according to the method of Hansen and Miller, Analytical Biochemistry, 7, 129 (1964).

The tubes are centrifuged at 3,000 rpm for five minutes. The supernatant is decanted and the Z-gel precipitate is counted in a Packard gamma scintillation spectrometer with a counting efficiency of approximately 60%.

The radiolabelled GCDFP-15 in the presence of 50 µl of bovine plasma solution (80 mg/ml) binds 30 percent of the counts present to the Z-gel. Addition of 100 µl of the 1:2,000 antibody solution to the assay causes 60% of the counts present to be bound to the Z-gel. A four-fold increase in antibody concentration will bind over 90% of the counts to the Z-gel. A standard antigen inhibition curve may be prepared for the assay and the quantity of inhibition of GCDFP-15 in a sample determined therefrom.

Analysis of 50 individual GCD fluid samples, using the above described radioimmunoassay, indicated a GCDFP-15 antigen concentration in the range of 1–10 mg/ml in unfractionated GCD fluid. Analysis of saliva samples from 20 different normal patients (12 women and 8 men) demonstrated an antigen range of 10–70 µg/ml of GCDFP-15. Human plasma samples from 92 normal women were found to have an antigen range of 5–85 ng/ml with a mean of 31 ng/ml. A study of 1,000 different patients including 300 patients with breast carcinoma has resulted in finding elevated plasma levels, up to 30,000 ng/ml, only for women with metastatic breast carcinoma.

Radioimmunoassay analysis of tissue culture supernatant fluids from four day cultures of explants of human breast carcinoma has demonstrated that approximately one third of these cultures release significant quantities of the GCDFP-15 protein as seen in Table I.

TABLE I

| Pathological Sample | GCDFP-15 in ng/ml | | | | | |
|---|---|---|---|---|---|---|
| | 1 | 2 | 3 | 4 | 5 | 6 |
| Fibroadenoma | 0 | 0 | 0 | 0 | 0 | 0 |
| Fibroadenoma | 0 | 0 | 0 | 0 | 0 | 0 |
| Fibroadenoma | 0 | 0 | 0 | 0 | 0 | 0 |
| Fibroadenoma | 0 | 0 | 0 | 0 | 0 | 0 |
| Fibrosis | 0 | 0 | 0 | 0 | 0 | 0 |
| Fibrosis | 43 | 36 | 79 | 25 | 44 | 25 |
| Sclerosing Adenosis | 145 | 145 | 185 | 90 | 160 | 170 |
| Gross Cystic Disease | 500 | 175 | 80 | 260 | 135 | 160 |
| Gross Cystic Disease | 2210 | 2158 | 1482 | 2392 | 1976 | 1430 |
| Dysplasia | 0 | 0 | 0 | 0 | 0 | 0 |
| Breast Carcinoma | 225 | 100 | 130 | 200 | 80 | 185 |
| Breast Carcinoma | 1040 | 1170 | 2470 | 1144 | 1170 | 1430 |
| Breast Carcinoma | 180 | 185 | 155 | 115 | 135 | 135 |
| Breast Carcinoma | 90 | 132 | 122 | 74 | 108 | 114 |
| Breast Carcinoma | 0 | 0 | 0 | 0 | 0 | 0 |
| Breast Carcinoma | 0 | 0 | 0 | 0 | 0 | 0 |
| Breast Carcinoma | 53 | 70 | 61 | 46 | 35 | 36 |
| Breast Carcinoma | 0 | 0 | 0 | 0 | 0 | 0 |
| Breast Carcinoma | 20 | 15 | 15 | 28 | 13 | 21 |
| Breast Carcinoma | 0 | 0 | 0 | 0 | 0 | 0 |

*Each sample of tissue was divided into approximately 20 mgs of tissue for culture in petri dishes containing 1 ml of culture media. Each sample was cultured in six replicate dishes. The culture media from each specimen was removed after four days and analyzed for GCDFP-15 content. All tissues were extensively rinsed in culture media prior to culturing.

Benign breast disease specimen culture demonstrated significant release of the GCDFP-15 from gross cystic disease tissue and sclerosing adenosis tissue (an epithelial proliferation associated with cystic disease).

While the aforesaid radioimmunoassay procedure for detecting GCDFP-15 in biological fluids has been described in some detail, the method of the present invention is not limited to any specific immunoassay procedure.

Thus, in its broadest aspect, the present method is useful for detecting the presence of GCDFP-15 in biological fluids using the GCDFP-15 specific antibody and labelled GCDFP-15. Such labelled GCDFP-15 includes the radiolabelled GCDFP-15 compounds hereinbefore described, preferably $^{125}$I-GCDFP-15, or GCDFP-15 labelled with any other unique and detectable label such as, for example, an electron spin resonance group (see U.S. Pat. Nos. 3,453,288, 3,481,952 and 3,507,879), or with chromophore groups, fluorophor groups, enzymes, red blood cells, latex particles and the like, using techniques and procedures well known in the diagnostic field.

Similarly, other radioimmunoassay procedures other than the Z-gel procedure specifically described herein may be employed by one skilled in the art to effect assay of the GCDFP-15 component. Thus, both biased and competitive binding type radioimmunoassay procedures may be employed in the practice of this invention.

The clinical utility of the GCDFP-15 plasma assay is further defined and compared to CEA as a tumor marker.

The CEA assay was performed with the CEA-Roche reagents as described by Hansen et al., Human Pathol., 5,139 (1974).

Plasma samples for analysis on both assays were obtained as single 7 cc K$_3$ ethylenediamine tetra-acetic acid blood tubes and were processed to plasma within three hours of obtaining the blood sample. The plasma samples were frozen at −20° C. until analysis. Clinic patients had plasma samples obtained prior to physical examination and specific therapy. The entire patient population studies consisted of 92 normal women and 768 patients with breast diseases being treated either at Columbia Presbyterian Medical Center or Duke University Medical Center. The patients are categorized as follows: 253 women with benign breast diseases; 164 women with Columbia Clinical Classification Stage A or B breast carcinoma; 288 women under observation after mastectomy for primary breast carcinoma; included in this group are 107 women from the above Columbia Clinical Classification Stage A or B breast carcinoma patients on whom blood samples have been obtained postoperatively; 216 women with metastatic breast carcinoma; included in this group are 46 women from the above postmastectomy observation group in whom metastatic disease developed; the other 170 metastatic breast carcinoma patients had developed metastatic disease prior to initiation of CEA and GCDFP-15 analysis.

Both the CEA and GCDFP assays have previously been found to be insensitive for detection of early breast carcinoma (Columbia Clinical Classification Stage A or B breast carcinoma). The utility of both assays has thus been assessed relative to metastatic carcinoma. A total of 288 patients with breast carcinoma have been followed after mastectomy. Forty-six of the 288 patients have developed metastatic recurrence of breast carcinoma. A stratification of CEA and GCDFP-15 plasma levels for these 46 patients is presented in Table II.

TABLE II
PATIENTS WHO UNDER OBSERVATION AFTER MASTECTOMY DEVELOPED METASTATIC BREAST CARCINOMA*

| LOCATION OF METASTASIS | NUMBER OF PATIENTS | GCDFP-15 >150 ng/ml ONLY | CEA >10 ng/ml ONLY | BOTH MARKERS ELEVATED | TOTALS |
|---|---|---|---|---|---|
| SOFT TISSUE | 14 | 0 | 3 (21%) | 0 | 3 (21%) |
| OSSEOUS | 17 | 5 (29%) | 6 (35%) | 0 | 11 (65%) |
| VISCERAL | 15 | 3 (20%) | 4 (27%) | 1 (7%) | 8 (53%) |
|  | 46 | 8 (17%) | 13 (28%) | 1 (2%) | 22 (48%) |

*ANTIGEN ELEVATIONS DEVELOPED EITHER PRIOR TO OR CONCURRENT WITH THE DIAGNOSIS OF METASTATIC DISEASE

Of the 46 patients who developed breast carcinoma recurrence, 14 developed CEA levels above 10 ng/ml and 9 developed GCDFP-15 plasma levels above 150 ng/ml. Analysis of these 46 patients relative to the site of their recurrent disease and CEA or GCDFP-15 plasma levels demonstrated the highest percentage detection in patients with osseous metastasis (65%) and the lowest percentage detection in patients with soft tissue metastasis (21%). Twenty-two of the 46 patients (48%) developed either abnormal CEA or GCDFP-15 plasma levels; only one of the 22 patients had elevated plasma levels of both CEA and GCDFP-15. Thus, utilization of both plasma marker assays as monitors for breast carcinoma recurrence was more effective than utilization of either assay alone.

The utility of the GCDFP-15 or CEA assay to detect recurrence of breast carcinoma prior to clinical demonstration of recurrence is illustrated by the following case report where the GCDFP-15 assay demonstrated increasing abnormal levels of this antigen for approximately one year prior to clinical detection of recurrence.

Case Report 1, Duke Study Number D-87

This patient, a 68 year old female, underwent left radical mastectomy in April 1975. Infiltrating duct carcinoma with metastases to eight of sixteen axillary lymph nodes was found. A right simple mastectomy was performed at the same time with no pathology found in the right breast specimen. The patient was begun on adjuvant chemotherapy of Cytoxan, Methotrexate and 5-Fluorouracil (CMF) in June 1975. This adjuvant chemotherapy was continued for one year. Initiation of CEA and GCDFP-15 determinations was Oct. 9, 1975 (Day 0). In November 1976 (Day 397) the patient developed left hip pain for the first time. A bone scan demonstrated increased tracer activity in the neck of the left femur and a chest x-ray indicated a left pleural effusion and several small nodules in the left lung.

The GCDFP-15 plasma assay had been progressively increasing above 150 ng/ml for almost one year since December 1975 (Day 55) and had risen to 6000 ng/ml by November 1976 (Day 397). The patient was treated with Diethylstilbestrol and had an objective remission with complete resolution of the left pleural effusion and left lung nodules. She also had marked subjective improvement with resolution of left hip pain.

However, in February 1977 (Day 485) she developed sudden shortness of breath and the diagnosis of pulmonary embolus was made clinically and supported by lung scan. She responded well to heparin anticoagulation and was begun again on Diethylstilbestrol along with Salicylate therapy approximately three weeks (Day 510) after her pulmonary embolus. Her chest x-ray remains clear and her left leg remains asymptomatic although there has been no change by x-ray in the lytic disease located in the left femur. The patient's most recent GCDFP-15 plasma level taken in June of 1977 (Day 590) was 315 ng/ml. The CEA plasma levels in this patient have constantly been below 5 ng/ml and without significant variation.

Two hundred and sixteen patients treated for metastatic breast carcinoma have been evaluated with serial plasma assays for both CEA and GCDFP-15. The 216 patients have been stratified for evaluation relative to the location of their metastatic disease as best determined by clinical and radiological examination, as seen in Table III.

TABLE III
PATIENTS UNDER TREATMENT FOR METASTATIC BREAST CARCINOMA

| LOCATION OF METASTASIS | NUMBER OF PATIENTS | GCDFP-15 >150 ng/ml ONLY | CEA >10 ng/ml ONLY | BOTH MARKERS ELEVATED | TOTALS |
|---|---|---|---|---|---|
| SOFT TISSUE | 73 | 8 (11%) | 11 (15%) | 0 | 19 (26%) |

TABLE III-continued
PATIENTS UNDER TREATMENT FOR METASTATIC BREAST CARCINOMA

| LOCATION OF METASTASIS | NUMBER OF PATIENTS | GCDFP-15 >150 ng/ml ONLY | CEA >10 ng/ml ONLY | BOTH MARKERS ELEVATED | TOTALS |
|---|---|---|---|---|---|
| OSSEOUS | 62 | 18 (29%) | 15 (24%) | 16 (26%) | 49 (79%) |
| VISCERAL | 81 | 12 (15%) | 18 (22%) | 13 (16%) | 43 (53%) |
| TOTALS | 216 | 38 (18%) | 44 (20%) | 29 (13%) | 111 (51%) |

Elevations in CEA (above 10 ng/ml) and in GCDFP-15 (above 150 ng/ml) have occurred at some point in the disease course of 111 (51%) of the 216 patients. Of these 111 patients, 44 (20%) had CEA elevations only, 38 (18%) had GCDFP-15 elevations only, and 29 (13%) had elevations of both CEA and GCDFP-15. Thus, the CEA and GCDFP-15 plasma antigen markers were elevated independently of one another in 74% of these patients. Of the 62 patients with an osseous location of metastatic disease, 49 (79%) had elevated plasma levels of either CEA or GCDFP-15. Of the 81 patients with visceral metastasis, 43 (53%) had elevated marker antigen levels, and 19 (26%) of the 73 patients with soft tissue metastasis had elevated values.

Of the 29 patients with both CEA abd GCDFP-15 plasma marker elevations, several had a much higher concentration of one antigen relative to the other. It has been observed that the more elevated plasma antigen is usually the best marker to follow as an indicator of therapeutic efficacy. An example case follows.

Case Report 2, Duke Study Number D-601

This patient, a 60 year old female, presented with a lump in the left breast of "six months" duration. Breast carcinoma fixed to the chest wall was found associated with large firm axillary lymph nodes. The patient underwent a left mastectomy in September 1975. Estrogen receptor analysis of the carcinoma specimen was positive. By January 1976, supraclavicular lymph node metastases were evident. Initiation of CEA and GCDFP-15 determinations was February 10, 1977 (Day 0). The patient was started on Aminoglutethimide therapy Feb. 13, 1977 (Day 3). Bone and liver scans at this time were negative. A left pleural effusion was present on chest x-ray, however, no discrete pulmonary nodules were seen and no osseous metastases were present. The patient's CEA was 7.0 ng/ml and the GCDFP-15 was 2250 ng/ml.

By March 1977 (Day 42) an increase in the left pleural effusion had occurred. The CEA had risen to 8.6 ng/ml and the GCDFP-15 had risen to 3,350 ng/ml. The patient was discontinued from Aminoglutethimide and admitted to the hospital for treatment of the left pleural effusion. By april 1977 (Day 60) a malignant pericardial effusion was documented. The CEA was 9.8 ng/ml and the GCDFP-15 was 4,900 ng/ml. Two weeks later the patient died from metastatic disease. The CEA two days before death (Day 72) was 10.5 ng/ml, the GCDFP-15 was 7,500 ng/ml.

Fifty-five of the 216 patients with metastatic breast carcinoma had estrogen receptor analysis performed on a biopsy specimen of their metastasis. These 55 patients have been analyzed relative to positive (>3 fm/mg estrogen receptor) or negative estrogen receptor content and whether they have developed either abnormal CEA or GCDFP-15 plasma levels. No association was seen for either CEA or GCDFP-15 plasma level alterations with estrogen receptor content of the breast carcinoma tissue.

Fifty-seven of the 216 patients with metastatic breast carcinoma have been followed with serial CEA and GCDFP-15 plasma level determinations to within two months of their death from metastatic disease. Analysis of these 57 patients relative to development of abnormal CEA or GCDFP-15 plasma levels indicated 63% developed CEA levels above 10 ng/ml and 45% developed GCDFP-15 plasma levels above 150 ng/ml. These two percentage figures are thus representative of the total percentage detection of abnormal CEA or GCDFP-15 levels which would occur during the course of metastatic disease.

An age distribution analysis for the 216 patients with metastatic breast carcinoma relative to the percentage of patients within each age group who had abnormal plasma levels of either CEA or GCDFP-15 was made. The percentage of abnormal plasma levels of CEA was slightly higher in the lower age groups whereas the percentage of abnormal plasma levels of GCDFP-15 was slightly higher in the upper age groups. The total range was from 31 to 80 years with detection of both antigens in all age groups.

As with the CEA assay, the serial measurement of GCDFP-15 levels in patients with metastatic breast carcinoma appeared to be useful in monitoring the efficacy of therapeutic regimens. For hormonal therapy, alterations in the GCDFP-15 plasma levels have accurately reflected clinical responsiveness with increasing levels indicative of progression and decreasing levels indicative of regression. Patients who show a decrease in the GCDFP-15 plasma level demonstrated objective disease regression or stabilization, whereas those patients with increasing plasma levels demonstrated disease progression.

Utilization of both the CEA and GCDFP-15 assays allowed detection of 22 (48%) of the 46 breast carcinoma recurrences in 288 patients under observation after mastectomy. The two assays were found to be almost completely independent of one another in this patient group, with only one of the 22 detected patients having both marker proteins elevated.

Thus, the two plasma marker proteins, CEA and GCDFP-15, both appear to be useful as monitors for the detection of metastatic breast carcinoma and for assessing the effectiveness of therapeutic regimens in patients with metastatic disease.

In a further aspect of the present invention GCDFP-15 levels in biological fluids is assayed using a double antibody radioimmunoassay where the second antibody is supported on an insoluble support material. The second antibody is elicited in a host animal of a different species than that in which the first antibody was produced. This aspect is exemplified in a test performed on amniotic fluid to determine the maturity of the fetus and the possible risk of respiratory distress syndrome in the delivered baby.

One hundred and eleven amniotic fluid samples were obtained by amniocentesis from pregnant women with gestational age fetuses of 16 to 42 weeks. The 111 amniotic fluid samples have been analyzed for GCDFP-15 content in the following manner.

The amniotic fluid samples were centrifuged at 1000 X G for five minutes. The supernatants were decanted and used for analysis.

Polypropylene tubes are used for the reaction. Five hundred ul of 0.1 M ammonium acetate buffer, pH 6.75, containing 1 mg/ml crystallized human albumin is added to each tube. The GCDFP-15 antigen standard for the radioimmunoassay is a 1:1,000 dilution of a 0.5 mg/ml solution of purified GCDFP-15. This standard is made up in 0.1 M ammonium acetate buffer, pH 6.75, containing 1 mg/ml crystallized human albumin. For the assay, five antigen inhibition curve tubes (in duplicate) receive 0 ul, 25 ul, 50 ul, 75 ul, and 100 ul, respectively of the GDCFP-15 antigen standard which is equivalent to 0 ng, 12.5 ng, 25 ng, 37.5 ng, and 50 ng of the GDCFP-15. Experimental tubes (in duplicate) receive 50 ul of amniotic fluid sample.

All assay tubes simultaneously receive 100 ul of a 1:10 dilution of stock $^{125}$I radiolabelled GCDFP-15 and 100 ul of a 1:2,000 dilution of antiserum. The addition procedure requires immediate mixing of the added $^{125}$I radiolabelled GCDFP-15 and added antiserum with the test sample. This is easily accomplished with automatic pipetting devices commercially available such as the Packard Prias automatic diluter. The assay tubes are incubated at room temperature for three hours. The reaction is stopped by addition of a second antibody attached to a solid phase bead. The second antibody is typically goat anti-rabbit IgG attached to Kynar as a 2% solid bead suspension in phosphate buffered saline pH 7.0, with 1% bovine albumin. The quantity of second antibody added is sufficient to complex between 5 and 10 ug of antibody. Typically 0.5 ml of Kynar suspension is added to each tube. The assay tubes are incubated at room temperature for 10 minutes then centrifuged at 3000 RPM for five minutes. The supernatant is decanted and the second antibody solid phase pellet counted in a Packard gamma scintillation spectrometer with a counting efficiency of approximately 60%.

The radiolabelled GCDFP-15 in the presence of albumin buffer only has approximately 5% of the counts precipitated by the solid phase second antibody. Addition of 100 ul of the 1:2,000 rabbit anti-GCDFP-15 antibody solution to the assay caused 60% of the counts present to be precipitated by the goat anti-rabbit solid phase second antibody. Addition of cold standard GCDFP-15 up to 50 ng to the assay results in a curvalinear inhibition curve of decreasing amount of counts bound to the second antibody solid phase pellet.

With the above assay, levels of GCDFP-15 in amniotic fluid between 0-1,000 ng/ml can be determined in approximately four hours time.

The level of GCDFP-15 in the 111 amniotic fluid samples relative to various ages of gestation is depicted in Table IV.

TABLE IV

| LEVEL OF GCDFP-15 IN AMNIOTIC FLUID | | | |
|---|---|---|---|
| Weeks of Gestation | Number of Specimens | Range of Level (ng/ml) | Mean Level (ng/ml) |
| 0-24 | 20 | 0-20 | 3 |
| 25-28 | 4 | 85-585 | 321 |
| 29-32 | 7 | 250-1350 | 665 |
| 33-36 | 41 | 250-4070 | 979 |
| 37-42 | 39 | 380-7900 | 2090 |

In thirty women amniotic fluid samples were obtained within 72 hours of delivery. Only four of the 30 samples had GCDFP-15 levels below 700 ng/ml. Two of the thirty women delivered babies which developed respiratory distress syndrome. The amniotic fluid samples from these two women had GCDFP-15 levels of 550 and 520 ng/ml. The outer two women with GCDFP-15 plasma levels below 700 delivered babies which did not develop any respiratory problems.

Six women have had serial amniotic fluid samples analyzed for GCDFP-15 levels. The samples were obtained between 28 and 37 weeks gestation. All six women had loglinear increasing levels of GCDFP-15 with increasing age of gestation. The doubling time of GCDFP-15 level in amniotic fluid was from 10 to 14 days. Extrapolation backward to a 0 level of GCDFP-15 gave a gestation age of 22-24 weeks.

The presence of GCDFP-15 in amniotic fluid appears to be a fetal product of third trimester (from 24 weeks to term). The level of GCDFP-15 increases in a loglinear fashion towards term. Amniotic fluid levels below 700 ng/ml are correlated with fetal birth which is associated with an increased risk of respiratory distress syndrome.

Another biological fluid other than plasma in which it is useful to analyze for GCDFP-15 content is urine from metastatic breast carcinoma patients. One hundred and four of the 216 patients with metastatic breast carcinoma have had urine sample analysis for GCDFP-15 level. The urine analysis has been carried out methodologically in an identical manner to the amniotic fluid analysis. Sixty-eight of the 104 patients had plasma GCDFP-15 levels below 150 ng/ml, and all 68 patients had urine levels of GCDFP-15 below 150 ng/mg urine creatinine. Thirty-six of the metastatic breast carcinoma patients had plasma GCDFP-15 levels about 150 ng/ml (range from 150 ng to 30,000 ng/ml). Twenty-two of these 36 patients had urine GCDFP-15 levels above 150 ng/mg urine creatinine (range 150 ng to 20,000 ng/mg urine creatinine).

Urine analysis of 94 patients after operation for primary breast carcinoma who were without clinical evidence of recurrence and who had GCDFP-15 plasma levels below 150 ng/ml found all 94 patients had urine GCDFP-15 levels below 150 ng/mg urine creatinine. Serial urine sample analysis on 10 normal women has demonstrated no urine levels of GCDFP-15 above 150 ng/mg urine creatinine.

A fairly close correlation exists between the plasma GCDFP-15 level and the urine GCDFP-15 level. The 15 patients which had plasma GCDFP-15 levels above 1000 ng/ml also had GCDFP-15 urine levels above 150 ng/mg urine creatinine. An example case of correlation between plasma and urine GCDFP-15 levels follows:

Duke Study Number D-115

This fifty-four year old patient underwent a mastectomy for breast carcinoma in 1973. In July 1975 metastasis was demonstrated in the mandible. The patient was treated with Cytoxan, Methotrexate and 5-Fluorouracil until March 1976 when the patient developed significant leukopenia and therapy was changed to Halotestin. The patient's initial GCDFP-15 plasma level taken in October 1975 was 60 ng/ml. By November 1976 the plasma level was 190 ng/ml. Advancement of osseous metastasis was noted at this time and the patient was restarted on CMF chemotherapy with continuation of Halotestin therapy. Four months later in February 1977 the GCDFP-15 plasma level was 1060 ng/ml and chemical therapy was discontinued. The patient received six weeks of radiation therapy to the low back and pelvic area for osseous metastases. In April 1977 the patient was initiated on Megace. Her GCDFP-15 plasma level was 1320 ng/ml. At this time the first GCDFP-15 urine level was obtained and was 270 ng/mg urine creatinine. Six weeks later the plasma GCDFP-15 level had risen to 2460 ng/ml and the urine GCDFP-15 level had risen to 410 ng/mg urine creatinine. The patient was discontinued from Megace and received a second course of radiation therapy to the lower half of her body. At the end of radiation therapy in July 1977 her plasma GCDFP-15 level was 4000 ng/ml and her urine GCDFP-15 was 1000 ng/mg urine creatinine. She was placed on Prednisone oral therapy and Cytoxan, Methotrexate and 5-Fluorouracil I.V. therapy. Two weeks later her plasma GCDFP-15 level had fallen to 2640 ng/ml and the urine GCDFP-15 level to 650 ng/mg urine creatinine. Her most recent GCDFP-15 plasma level in September 1977 was 2,100 ng/ml and the urine GCDFP-15 level was 520 ng/mg urine creatinine.

Preparation of the goat anti-rabbit IgG second antibody supported on the Kynar support material can be accomplished as follows. The starting material is unsintered Kynar (vinylidene fluoride) resin powder, grade 301 F, Pennwalt Corp. The powder is dispersed in isopropanol (2-propanol) in the proportions of 50 grams Kynar in 1000 ml of isopropanol. The suspension is then homogenized by a Brinkmann Polytrol for 5 minutes at a pulse-frequency of 4000 c.p.s. The Kynar-isopropanol mixture is then transferred to a cylinder containing ten liters of saline and stirred until dispersed. The Kynar is then allowed to settle out and most of the supernatant is decanted. After two water washes, the Kynar is resuspended in phosphate buffered saline (PBS) (pH 7.0) with merthiolate (0.01%) to yield a 2% Kynar concentration. The Kynar is now in the activated state and able to accept protein. Serum from goats immunized against rabbit IgG was pooled and found to contain 13.72 mg/ml precipitable antibody protein. While the isopropanol activated Kynar is stirring, 0.25 to 1 ml of undiluted antiserum per gram of Kynar is added. The mixture is then homogenized again by the polystron for 5 minutes at the same pulse-frequency as before. The suspension is then continuously stirred at room temperature for a minimum of 6 hours followed by stirring at 4° C. for a minimum of 12 hours. The suspension is now ready to be washed. This is accomplished by centrifugation at 1500 x g for 10 minutes followed by resuspension in PBS (pH 7.0). This process is repeated once more and the final material resuspended in PBS (pH 7.0) to 20 grams of Kynar per 1000 ml of buffer. The mixture is again stirred and 0.05 to 0.25 ml of bovine serum albumin per gram of Kynar added. Homogenization with the Polytron at 4000 c.p.s. for 5 minutes is the final step in this procedure.

Additional disclosure concerning the preparation and use of Kynar as a solid support for protein materials is found in U.S. Pat. No. 3,843,443. A more general description of second antibodies supported on insoluble supports in provided in U.S. Pat. No. 4,048,298.

I claim:

1. A method useful in determining the maturity of a fetus which method comprises determining the concentration of the glycoprotein gross cystic disease fluid protein-15 (GCDFP-15) in an amniotic fluid sample by conducting an immunoassay for said glycoprotein in said amniotic sample utilizing a GCDFP-15 selective antibody and GCDFP-15 labelled with a unique and detectable label to produce an antigen-antibody reaction product, separating said product from the said reagents and determining the concentration of GCDFP-15 in the amniotic fluid sample by detecting the quantitative value of said label in either said reaction product or said reagents and comparing said label value to a standard curve whereby the concentration of GCDFP-15 in said amniotic fluid is directly correlatable to the maturity of said fetus after about 24 weeks of gestation wherein said GCDFP-15 is characterized as follows:
   (a) a glycoprotein having a calculated monomer size of about 15,000 daltons as determined by sodium dodecyl sulfate acrylamide gel analysis; and
   (b) immunologically not identical to any components of plasma as determined by Ouchterlony analysis; and
   (c) immunological cross identity with a component of human milk and human saliva; and
   (d) cleavage with cyanogen bromide provides two peptides one of which is blocked, and one of the peptides has a molecular weight of about 12,500 daltons as determined by sodium dodecyl sulfate acrylamide gel analysis and having the following partial sequence of amino acids:

$$\text{H}_2\text{N—Val-Val-Lys-Thr-Tyr-Leu-Ile-Ser-Ser-Ile-Pro-Leu}^{10}$$
$$\text{Gln-Gly-Ala-Phe-Asn-Tyr-Lys-Tyr-Thr-Ala-(Cys)-Leu-(Cys)-}^{30}$$
$$\text{Asp-Asp-Asn-Pro-Lys-Thr-Phe-Tyr-Trp-Asp-Phe-Tyr-Thr-(Gln)-}^{39}$$

( ) indicate possible derivitization.

2. The method of claim 1 wherein said amniotic fluid sample is obtained near the time of delivery and the concentration of GCDFP-15 found in said sample is compared to a pre-determined cut-off level whereby a concentration below said cut-off level is indicative of potential fetal immaturity with associated respiratory distress syndrome in the delivered baby.

3. The method of claim 1 wherein said immunoassay is a radioimmunoassay and said labelled GCDFP-15 is GCDFP-15 labelled with a radioactive isotope.

4. The method of claim 3 wherein said radioactive isotope is $^{125}$I.

5. The method of claim 3 wherein the antigen-antibody reaction is precipitated, the counts of the precipitate detected and the amount of GCDFP-15 in the amniotic fluid sample is determined from a standard inhibition curve.

* * * * *